US009295609B2

(12) United States Patent
Ukawa

(10) Patent No.: US 9,295,609 B2
(45) Date of Patent: Mar. 29, 2016

(54) CARDIOPULMONARY RESUSCITATION MONITORING APPARATUS

(75) Inventor: Teiji Ukawa, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 9 days.

(21) Appl. No.: 13/403,262

(22) Filed: Feb. 23, 2012

(65) Prior Publication Data

US 2012/0220900 A1 Aug. 30, 2012

(30) Foreign Application Priority Data

Feb. 24, 2011 (JP) ................................ 2011-038166

(51) Int. Cl.
*A61B 5/103* (2006.01)
*A61H 31/00* (2006.01)

(52) U.S. Cl.
CPC ............ *A61H 31/005* (2013.01); *A61H 31/007* (2013.01); *A61H 2201/5061* (2013.01); *A61H 2201/5079* (2013.01); *A61H 2201/5084* (2013.01)

(58) Field of Classification Search
USPC .................................... 33/511, 512; 600/587
See application file for complete search history.

(56) References Cited

U.S. PATENT DOCUMENTS 6,306,107 B1 * 10/2001 Myklebust et al. ........... 600/587
2008/0208082 A1 * 8/2008 Nysaether et al. ............ 600/595
2008/0300517 A1 * 12/2008 Nysaether ....................... 601/41
2010/0049266 A1 2/2010 Ochs et al.
2010/0204622 A1 * 8/2010 Hwang et al. .................. 601/41
2010/0228166 A1 * 9/2010 Centen ............................ 601/41
2012/0191014 A1 * 7/2012 Fossan .......................... 600/587

FOREIGN PATENT DOCUMENTS

EP 1997469 A1 12/2008
GB 2446605 A 8/2008
JP 2010509014 A 3/2010

OTHER PUBLICATIONS

Neurauter, Andreas et al. "Comparison of mechanical characteristics of the human and porcine chest during cardiopulmonary resuscitation", Resuscitation, Elsevier, IE, Apr. 1, 2009, vol. 80, No. 4, pp. 463-469.
Search Report issued May 30, 2012 by the European Patent Office in counterpart European Application No. 12156617.8.

* cited by examiner

*Primary Examiner* — Sean Dougherty
*Assistant Examiner* — Daniel Cerioni
(74) *Attorney, Agent, or Firm* — Sughrue Mion, PLLC

(57) ABSTRACT

A monitoring apparatus for cardiopulmonary resuscitation includes: an information acquiring section configured to acquire information of a force, displacement, and velocity during a compression of a chest of a living body; a calculating section configured to calculate viscoelasticity information of the chest based on the information of the force, displacement, and velocity, which are acquired by the information acquiring section; an evaluating section configured to perform evaluation related to the cardiopulmonary resuscitation by using the viscoelasticity information which is calculated by the calculating section; and an outputting section configured to perform an output showing the evaluation which is performed by the evaluating section.

10 Claims, 3 Drawing Sheets

CARDIOPULMONARY RESUSCITATION MONITORING APPARATUS

BACKGROUND OF THE INVENTION

The present invention relates to a monitoring apparatus for cardiopulmonary resuscitation which, in order to enable a rescuer or the like to perform an optimum cardiac massage maneuver when, for example, cardiopulmonary resuscitation is executed, monitors the massage.

In cardiac massage executed in cardiopulmonary resuscitation, conventionally, it is said that a compression displacement of about 4 to 5 cm is appropriate. Related-art apparatuses are known which determines whether the massage is optimally performed or not, and which informs a rescuer or the like of the determination. In several related-art apparatuses, one of or a combination of one or more of signals obtained from force, displacement, velocity, and acceleration sensors are used. For example, there is a related art in which a compression displacement is obtained by double integration of an acceleration, and an influence of common mode noises which are superimposed on the compression displacement because of relationships with a force is eliminated (see JP-T-2010-509014).

There is also a related art in which a rigidity function is obtained from a force and a displacement, and it is determined from its non-linearity whether a compression displacement is appropriate or not (see EP1997469A1). In the related art, in order to correctly obtain the rigidity function, the damping force component (viscosity component) which is proportional to the velocity is previously subtracted.

On the other hand, it is known that the thoracic which is an object of a compression in executed cardiac massage has viscoelasticity characteristics (Bankman et al IEEE TRANSACTIONS ON BIOMEDICAL ENGINEERING, VOL. 37, NO. 2, FEBRUARY 1990, P 211-217). Here, the viscosity is caused by movement of the organs in the thoracic due to the compression. In the case where an appropriate compression is performed, the viscosity is caused in addition to the elasticity.

In the relevant technique disclosed in JP-T-2010-509014, however, the viscosity of the chest which is the compression object is not considered in the determination whether a cardiac massage maneuver which is appropriate in relationships of the displacement and the force is performed or not. In the related art disclosed in EP1997469A1, the viscosity component is subtracted, and therefore the viscosity of the chest is not considered in the determination whether a cardiac massage maneuver is performed or not.

As described above, the thoracic which is the compression object has viscoelasticity characteristics, and hence the determination in which this is not considered is forced to be incorrect. In the case where cardiac massage for cardiopulmonary resuscitation is performed on a soft bed or in a rolling vehicle interior, for example, there is a possibility that it is impossible to determine whether the massage is appropriate in relationships of the displacement and the force or not.

SUMMARY

It is therefore an object of the invention to provide a monitoring apparatus for cardiopulmonary resuscitation which, in order to enable a rescuer or the like to perform an optimum cardiac massage maneuver, can monitor the massage.

In order to achieve the object, according to the invention, there is provided a monitoring apparatus for cardiopulmonary resuscitation, the monitoring apparatus comprising: an information acquiring section configured to acquire information of a force, displacement, and velocity during a compression of a chest of a living body; a calculating section configured to calculate viscoelasticity information of the chest based on the information of the force, displacement, and velocity, which are acquired by the information acquiring section; an evaluating section configured to perform evaluation related to the cardiopulmonary resuscitation by using the viscoelasticity information which is calculated by the calculating section; and an outputting section configured to perform an output showing the evaluation which is performed by the evaluating section.

The calculating section may calculate the viscoelasticity information by using a following expression:

$$f=Kx+Bx'+e$$

where f: the force, x: the displacement, x': the velocity, K: a coefficient of rigidity, B: a coefficient of viscosity, and e: external disturbance.

The calculating section may obtain the coefficient of rigidity K and the coefficient of viscosity B by a regression calculation.

The information acquiring section may include a force sensor and an acceleration sensor, the information acquiring section may acquire the information of the force by the force sensor, the information acquiring section may perform single integration of the acceleration obtained by the acceleration sensor to acquire the information of the velocity, and the information acquiring section may perform double integration of the acceleration to acquire the information of the displacement.

The information acquiring section may include a force sensor and a velocity sensor, the information acquiring section may acquire the information of the force by the force sensor, the information acquiring section may acquire the information of the velocity by the velocity sensor, and the information acquiring section may perform single integration of the velocity to acquire the information of the displacement.

The information acquiring section may include a force sensor and a displacement sensor, the information acquiring section may acquire the information of the force by the force sensor, the information acquiring section may acquire the information of the displacement by the displacement sensor, and the information acquiring section may perform first-order differentiation of the displacement to acquire the information of the velocity.

The calculating section may calculate at least one of a coefficient of viscosity and a time constant as the viscoelasticity information, and the evaluating section may perform the evaluation related to cardiopulmonary resuscitation by using the viscoelasticity information which is calculated by the calculating section and using at least one of a coefficient of rigidity and external disturbance.

When the information acquiring section acquires the information of the displacement or the information of the velocity by performing integration of the acceleration, the calculating section may correct an offset contained in a signal of the acceleration obtained by the acceleration sensor, so as to minimize external disturbance, thereby removing drift caused by integration of the offset.

The calculating section may use a signal of the acceleration in the vicinity of a timing when the force is maximum or minimum, thereby correcting the offset so that a correlation between the force and the displacement is maximum, and the external disturbance is minimum.

When at least one of the coefficient of rigidity, the coefficient of viscosity, the time constant, and the external disturbance exceeds a predetermined determination criterion, the evaluating section may perform the evaluation related to the cardiopulmonary resuscitation by using only the information of the force.

DETAILED DESCRIPTION OF EMBODIMENTS

Figure 1:
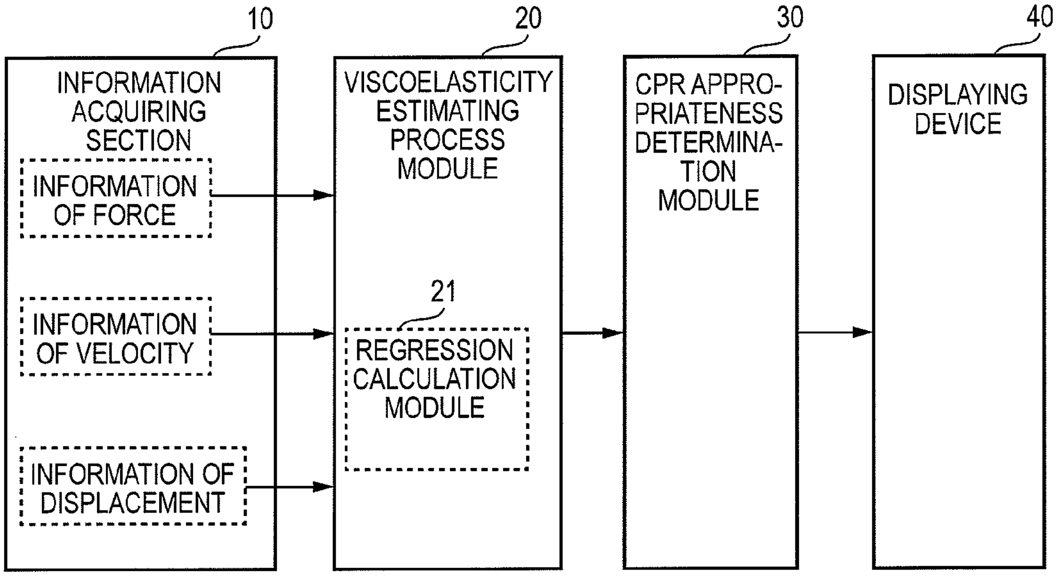
FIG. 1 is a block diagram showing an embodiment of the monitoring apparatus for cardiopulmonary resuscitation of the invention.

Hereinafter, an embodiment of the monitoring apparatus for cardiopulmonary resuscitation of the invention will be described with reference to the accompanying drawings. In the figures, the identical components are denoted by the same reference numerals, and duplicate description will be omitted. The monitoring apparatus for cardiopulmonary resuscitation of the embodiment can be configured as shown in FIG. 1. The monitoring apparatus for cardiopulmonary resuscitation includes an information acquiring section 10, a viscoelasticity estimating process module 20 which is a calculating section, a CPR (cardiopulmonary resuscitation) appropriateness determination module 30 which is an evaluating section, and a displaying device 40 which is an example of an outputting section. The displaying device 40 may be a device which shows characters by means of display such as an LED, or a device which outputs a message simply by lighting, that which outputs a message by means of an audio output, or that which outputs a message by a necessary combination of these means. The displaying device may be any kind of device as far as it performs an output showing the evaluation by the CPR appropriateness determination module 30.

Figure 2:
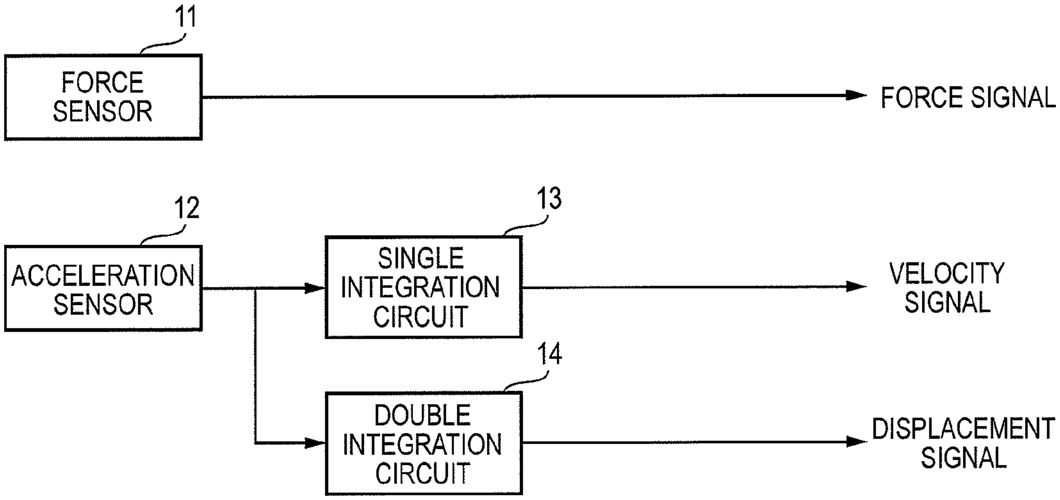
FIG. 2 is a block diagram showing a first example of the configuration of the embodiment of the monitoring apparatus for cardiopulmonary resuscitation of the invention.
Figure 3:
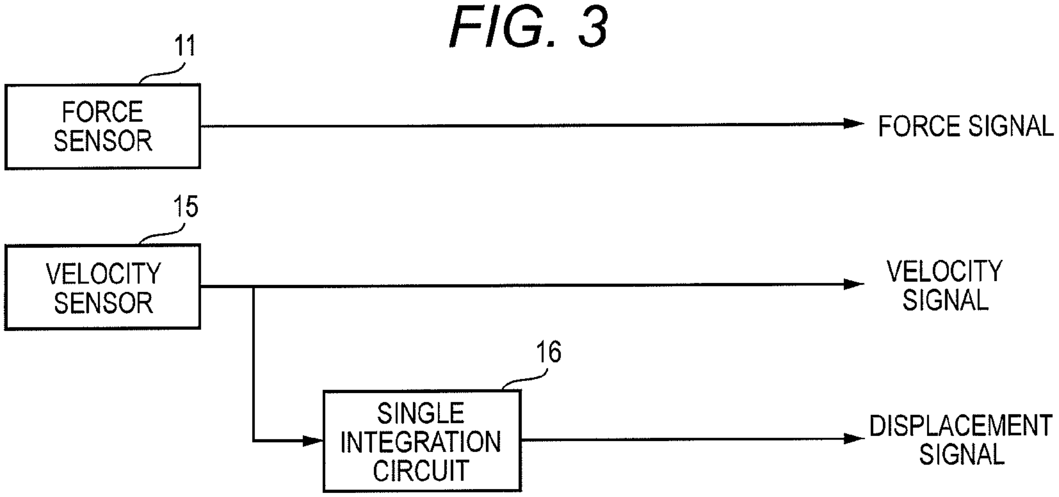
FIG. 3 is a block diagram showing a second example of the configuration of the embodiment of the monitoring apparatus for cardiopulmonary resuscitation of the invention.
Figure 4:
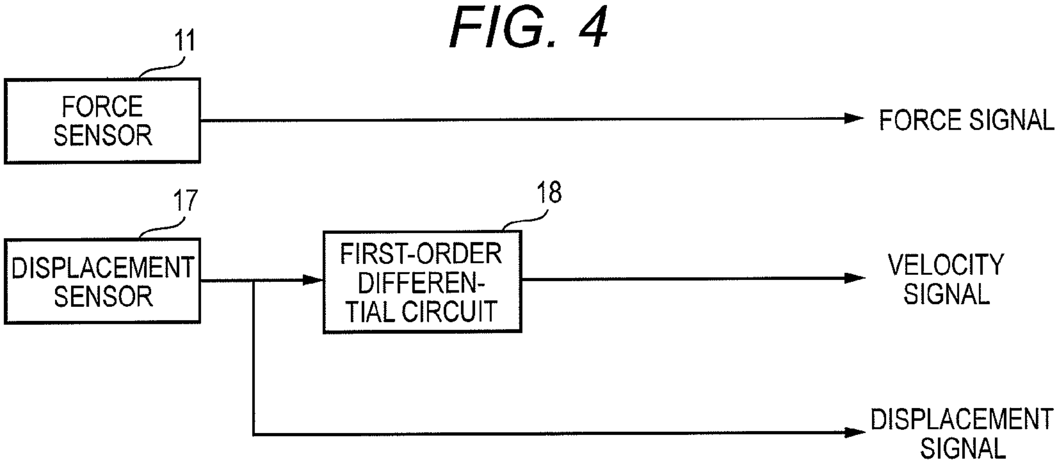
FIG. 4 is a block diagram showing a third example of the configuration of the embodiment of the monitoring apparatus for cardiopulmonary resuscitation of the invention.

The information acquiring section 10 acquires information of the force, the displacement, and the velocity during a chest compression, and can be realized by, for example, the configuration of any one of FIGS. 2 to 4. First, the configuration of FIG. 2 includes: a force sensor 11 which detects a force applied to the chest during compression of the chest of a living body; an acceleration sensor 12 which detects the acceleration; a single integration circuit 13; and a double integration circuit 14. The force sensor 11 outputs a signal indicating the detected force. The acceleration sensor 12 outputs an acceleration signal, the single integration circuit 13 performs a single integration of the acceleration to output a velocity signal, and the double integration circuit 14 performs a double integration of the acceleration to output a displacement signal.

The configuration of FIG. 3 includes the force sensor 11, a velocity sensor 15 which detects the velocity, and a single integration circuit 16. The velocity sensor 15 outputs a velocity signal, and the single integration circuit 16 performs a single integration of the velocity to output a displacement signal.

The configuration of FIG. 4 includes the force sensor 11, a displacement sensor 17 which detects the displacement, and a first-order differential circuit 18. The displacement sensor outputs a displacement signal, and the first-order differential circuit 18 performs a first-order differentiation of the displacement to output a velocity signal. In any of the configurations shown in FIGS. 2 to 4, in the transmission from the information acquiring section 10 to the viscoelasticity estimating process module 20, the information is converted to digital information, or to a form which can be processed by the viscoelasticity estimating process module 20 that is a computer.

The viscoelasticity estimating process module 20 calculates viscoelasticity information of the chest based on information of the force, the displacement, and the velocity acquired by the information acquiring section 10, and can be configured by, for example, a computer. Specifically, the viscoelasticity estimating process module 20 calculates viscoelasticity information by using the Voigt model indicated by following (Exp. 1):

$$f=Kx+Bx'+e \qquad \text{(Exp. 1)}$$

where f: the force, x: the displacement, x': the velocity, K: the coefficient of rigidity, B: the coefficient of viscosity, and e: the external disturbance.

The viscoelasticity estimating process module 20 includes a regression calculation module 21, and obtains the coefficient of rigidity K, the coefficient of viscosity B, the time constant B/K, and the external disturbance e by a regression calculation. For example, a multiple regression calculation of the displacement x and the velocity x' is performed on the force f to obtain the coefficient of rigidity K and coefficient of viscosity B which are optimum. The difference between a force which is estimated from the obtained coefficient of rigidity K and coefficient of viscosity B, and the measured force f is calculated as the external disturbance e.

In the case where the configuration of FIG. 2 is employed, the velocity signal is obtained by a single integration of the acceleration signal, and the displacement signal is obtained by a double integration of the acceleration signal. In this case, also unwanted offset noises which are contained in the acceleration signal are integrated, and drift occurs. There is a technique in which, in order to suppress drift occurring in an integration of an offset of an acceleration signal, the timing of starting an integration of an acceleration is determined by an output of a force sensor (EP1057451B1). Even when the timing of starting an integration of an acceleration is determined by an output of a force sensor, however, the problem in that drift occurs during one compression cannot be solved.

Figure 5:
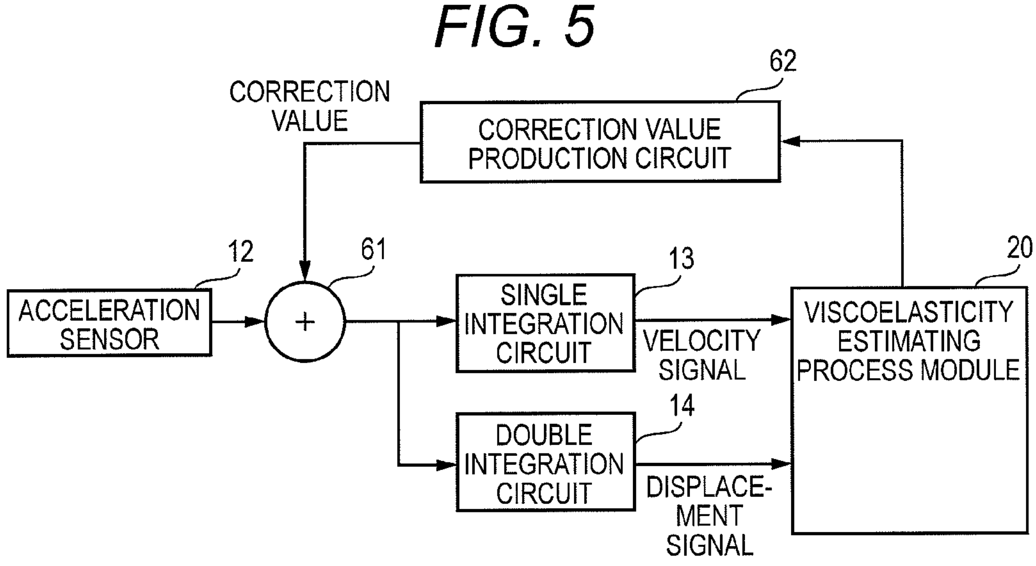
FIG. 5 is a block diagram showing a configuration example which corrects an offset of a signal obtained by an acceleration sensor of the embodiment of the monitoring apparatus for cardiopulmonary resuscitation of the invention.

In the embodiment, drift appears as the external disturbance e, and therefore the output of the acceleration sensor 12 is corrected so as to minimize the external disturbance e. FIG. 5 shows a configuration related to the correction. An addition circuit 61 is disposed on the side of the output of the acceleration sensor 12, and an output of the addition circuit 61 is given to the single integration circuit 13 and the double integration circuit 14. A correction value production circuit 62 is disposed. The correction value production circuit 62 fetches the external disturbance e from the viscoelasticity estimating process module 20, produces a correction value so that the external disturbance e becomes minimum, and gives the correction value to the addition circuit 61. When the external disturbance e is minimized by changing (increasing or decreasing) the correction value, the correction value production circuit 62 holds the correction value. This process may be performed in each sampling of the acceleration sensor 12.

During a chest compression, the velocity is low in the vicinity of a timing when the force is maximum or minimum, and therefore an influence of Bx' which is the viscosity term is small. When the viscosity is neglected, (Exp. 1) is expressed as following (Exp. 2):

$$f=Kx+e \quad \text{(Exp. 2)}$$

It will be seen that, when a measurement signal in the vicinity of a timing when the force is maximum or minimum is used, and the correlation between the force f and the displacement x is maximum, the external disturbance e is minimum. In the case where the process is performed by the configuration shown in FIG. 5, therefore, a measurement signal in the vicinity of a timing when the force is maximum or minimum, and the correction value production circuit 62 can operate so as to, when the external disturbance e is minimized by changing (increasing or decreasing) the correction value, hold the correction value. According to the configuration, the improvement of the accuracy can be easily realized while considering the viscosity.

As described above, the viscoelasticity estimating process module 20 calculates at least one of the coefficient of viscosity B and the time constant B/K, as viscoelasticity information, and the CPR appropriateness determination module evaluates the appropriateness of cardiopulmonary resuscitation by using the viscoelasticity information which is calculated by the viscoelasticity estimating process module 20, and, as required, at least one of the coefficient of rigidity K and the external disturbance e.

The CPR appropriateness determination module 30 has the upper and lower thresholds which define the range obtained from a living body, with respect to the coefficient of rigidity K, the coefficient of viscosity B, and the time constant B/K, and the upper threshold with respect to the external disturbance e. The CPR appropriateness determination module 30 further has the upper and lower thresholds of the displacement x which is perceived to be adequate in displacement during a compression in cardiac massage that is executed in cardiopulmonary resuscitation.

Figure 6:
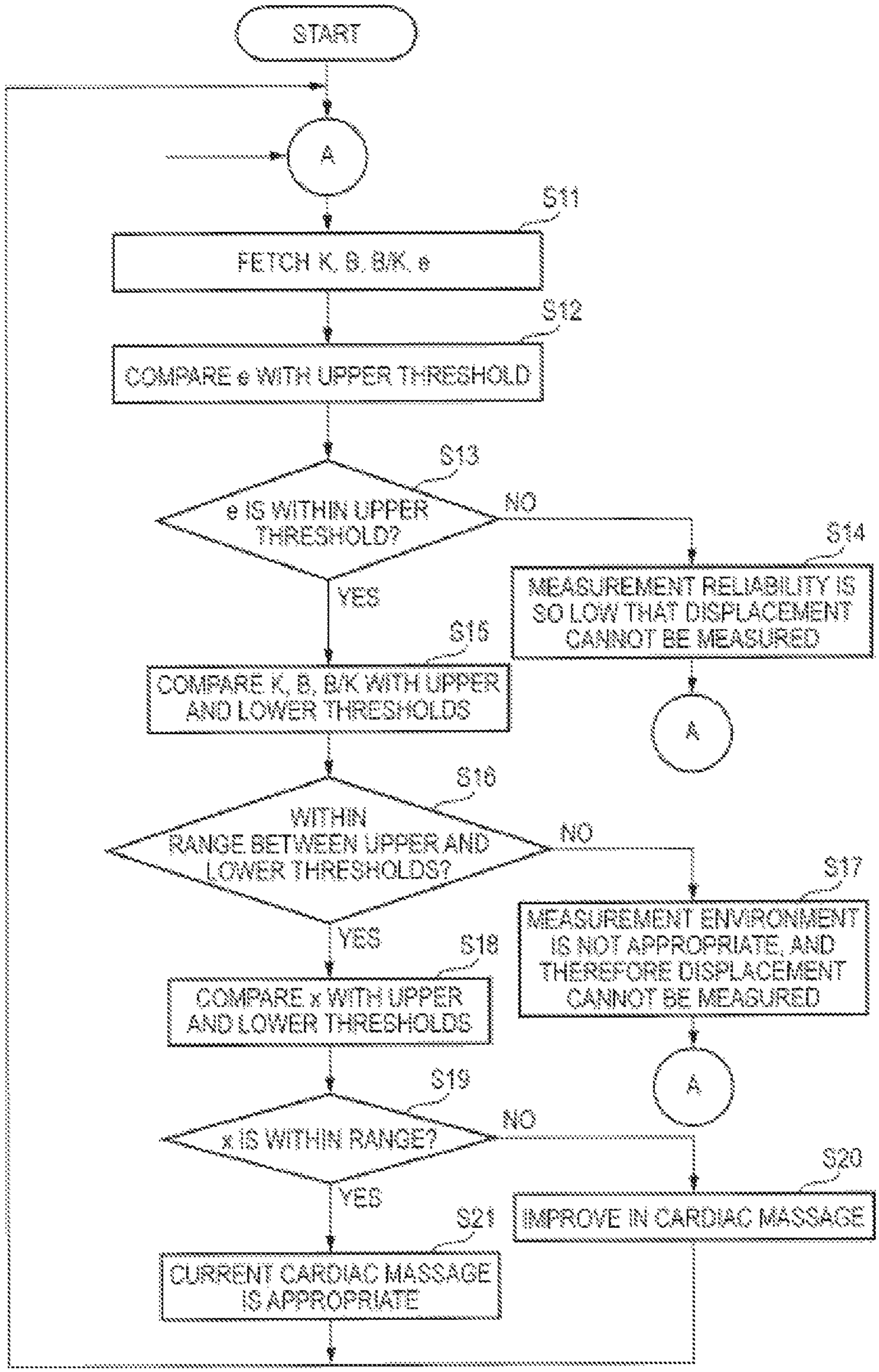
FIG. 6 is a flowchart showing the operation of the embodiment of the monitoring apparatus for cardiopulmonary resuscitation of the invention.

The CPR appropriateness determination module 30 operates on programs corresponding to the flowchart shown in FIG. 6, and therefore the operation will be described with reference to the flowchart. The CPR appropriateness determination module 30 receives the coefficient of rigidity K, the coefficient of viscosity B, the time constant B/K, and the external disturbance e from the viscoelasticity estimating process module 20 (S11), compares the external disturbance e with the upper threshold thereof (S12), and determines whether the measurement for the determination of appropriateness of CPR is performed within a reliable range or not (S13). If, as a result of the determination, the process branches to NO branch, it is determined that "MEASUREMENT RELIABILITY IS SO LOW THAT DISPLACEMENT CANNOT BE MEASURED," and display information of a message corresponding to the determination is sent to the displaying device 40 (S14).

By contrast, if step S13 branches to YES branch, the coefficient of rigidity K, the coefficient of viscosity B, and the time constant B/K are compared with their upper and lower thresholds which define the range obtained from a living body (S15), and it is determined whether they are within the range between the upper and lower thresholds or not (S16). If, as a result of the determination, the process branches to NO branch, it is determined that "MEASUREMENT ENVIRONMENT IS NOT APPROPRIATE, AND THEREFORE DISPLACEMENT CANNOT BE MEASURED," and display information of a message corresponding to the determination is sent to the displaying device 40 (S17).

If step S16 branches to YES branch, the displacement x is compared with its upper and lower thresholds (S18), and it is determined whether the displacement x is within the appropriate range or not (S19). If, as a result of the determination, the process branches to NO branch, it is determined that "IMPROVE IN CARDIAC MASSAGE," and display information of a message corresponding to the determination is sent to the displaying device 40 (S20).

By contrast, if step S19 branches to YES branch, it is determined that "CURRENT CARDIAC MASSAGE IS APPROPRIATE," and display information of a message corresponding to the determination is sent to the displaying device 40 (S21). In the embodiment, in this way, when cardiac massage is performed on a soft bed, for example, it is possible to automatically detect that the cardiac massage is performed on a soft bed, by using the fact that the coefficient of rigidity K, the coefficient of viscosity B, and the time constant B/K are largely different from the coefficient of rigidity K, the coefficient of viscosity B, and the time constant B/K of the original living body. In the case where it is detected that cardiac massage is performed on a bed which is unsuitable for cardiac massage, therefore, the displacement measurement is suppressed, and it is possible to prevent erroneous information from being provided to the rescuer. Although, in the embodiment, "THE MEASUREMENT ENVIRONMENT IS NOT APPROPRIATE" is displayed, a more specific suggestion such as that the bed should be changed may be provided.

In the case where it is detected that cardiac massage is performed on a bed, moreover, appropriateness determination may be performed based on only the force and without using information related to the displacement.

Furthermore, the measurement reliability may be informed depending on the degree of the external disturbance e. Moreover, it is possible to obtain K and B without being affected by the external disturbance e which is not correlated with a compression, such as vibrations, and instructions which are more correct may be given to the rescuer or the like.

According to an aspect of the invention, viscoelasticity information of the chest is calculated based on information of the force, the displacement, and the velocity, and evaluation related to cardiopulmonary resuscitation is performed by using the calculated viscoelasticity information. Therefore, appropriate evaluation in which it is considered that the thoracic that is the compression object has viscoelasticity characteristics is performed, and it is possible to guide the cardiac massage maneuver by the rescuer or the like to be correctly performed.

According to an aspect of the invention, K and B are obtained by a regression calculation. Therefore, an influence of the external disturbance e which is not correlated with a compression, such as vibrations of a vehicle can be eliminated, and K and B can be obtained. Furthermore, it is possible also to inform the measurement reliability depending on the degree of e.

According to an aspect of the invention, at least one of the coefficient of viscosity B and the time constant B/K is calculated as viscoelasticity information. Therefore, it is possible to detect that cardiac massage is performed on a soft bed, by using the fact that the coefficient of rigidity K, coefficient of viscosity B, and time constant B/K which are calculated in the case where cardiac massage is performed on a soft bed are largely different from the coefficient of rigidity K, the coefficient of viscosity B, and the time constant B/K of the living body, and further to perform necessary notification such as that an erroneous displacement is prevented from being informed to the rescuer or the like.

According to an aspect of the invention, offset noise correction is applied to the acceleration signal so as to minimize e, whereby drift can be suppressed. In the case where the acceleration is integrated to obtain the velocity and the displacement, it is possible to calculate an appropriate value.

According to an aspect of the invention, when at least one of the coefficient of rigidity K, the coefficient of viscosity B, the time constant B/K, and the external disturbance e exceeds a predetermined determination criterion, the appropriateness of cardiopulmonary resuscitation is evaluated by using only the force, whereby, even in the case where cardiac massage is performed on a soft bed, the effect of the cardiopulmonary resuscitation can be adequately evaluated.

What is claimed is:

1. A monitoring apparatus for cardiopulmonary resuscitation, the monitoring apparatus comprising:

- a processor that controls the monitoring apparatus to execute:
- an information acquiring section configured to measure force, a displacement, and a velocity of a compression of a chest of a living body;
- a calculating section configured to calculate through regression calculation both (i) a coefficient of rigidity of the chest and (ii) a coefficient of viscosity of the chest, using the force, the displacement, and the velocity, and to calculate an external disturbance, wherein the external disturbance is a difference between the force measured by the information acquiring section and an estimated force estimated using the regressively calculated coefficient of rigidity, the regressively calculated coefficient of viscosity, and the force, the displacement, and the velocity measured by the information acquiring section;
- an evaluating section configured to determine a reliability of an evaluation of the cardiopulmonary resuscitation using the external disturbance, the regressively calculated coefficient of rigidity, and the regressively calculated coefficient of viscosity calculated by the calculating section, the reliability of the evaluation determined by comparing the external disturbance to a maximum external disturbance threshold and comparing the regressively calculated coefficient of rigidity and the regressively calculated coefficient of viscosity to maximum and minimum reliability thresholds; and
- an outputting section configured to output a result indicating the reliability of the evaluation of the cardiopulmonary resuscitation, the result being based on the comparisons to the maximum external disturbance threshold and the maximum and minimum reliability thresholds,
- wherein the reliability is an indication of an accuracy of the cardiopulmonary resuscitation to a user of the monitoring apparatus such that the user maintains or adjusts the displacement of the cardiopulmonary resuscitation of the chest of the living body based on the indication.

2. The monitoring apparatus according to claim 1, wherein the calculating section calculates the coefficient of rigidity of the chest, the coefficient of viscosity of the chest, and the external disturbance by using the expression:

$$f=Kx+Bx'+e$$

where f: the force, x: the displacement, x': the velocity, K: the coefficient of rigidity, B: the coefficient of viscosity, and e: the external disturbance.

3. The monitoring apparatus according to claim 2, wherein the calculating section regressively calculates the coefficient of rigidity of the chest and the coefficient of viscosity of the chest at each sampling of the information of the force, the displacement, and the velocity by the information acquiring section.

4. The monitoring apparatus according to claim 1, wherein:

the information acquiring section comprises a force sensor and an acceleration sensor, the information acquiring section measures the force using the force sensor, the information acquiring section performs single integration of the acceleration obtained by the acceleration sensor to measure the velocity, and the information acquiring section performs double integration of the acceleration to measure the displacement.

5. The monitoring apparatus according to claim 1, wherein:

the information acquiring section comprises a force sensor and a velocity sensor, the information acquiring section measures the force using the force sensor, the information acquiring section measures the velocity using the velocity sensor, and the information acquiring section performs single integration of the velocity to measure the displacement.

6. The monitoring apparatus according to claim 1, wherein:

the information acquiring section comprises a force sensor and a displacement sensor, the information acquiring section measures the force using the force sensor, the information acquiring section measures the displacement using the displacement sensor, and the information acquiring section performs first-order differentiation of the displacement to measure the velocity.

7. The monitoring apparatus according to claim 1, wherein the calculating section calculates a time constant from the regressively calculated coefficient of rigidity and the regressively calculated coefficient of viscosity, and the evaluating section determines the reliability of the evaluation of the cardiopulmonary resuscitation by comparing the time constant to a reliability threshold.

8. The monitoring apparatus according to claim 4, wherein, when the information acquiring section measures the displacement or the information of the velocity by performing integration of the acceleration, the calculating section corrects the external disturbance contained in a signal of the acceleration obtained by the acceleration sensor, to minimize the external disturbance, and removing a drift caused by integration of the external disturbance.

9. The monitoring apparatus according to claim 8, wherein the calculating section uses a signal of the acceleration in the vicinity of a timing when the force is maximum or minimum, and corrects the offset so that a correlation between the force and the displacement is maximum, and the external disturbance is minimum.

10. The monitoring apparatus according to claim 7, wherein, when at least one of the regressively calculated coefficient of rigidity or the regressively calculated coefficient of viscosity exceeds the maximum or minimum reliability thresholds, the time constant exceeds the reliability threshold, and the external disturbance exceeds the maximum external disturbance threshold, the evaluating section evaluates the cardiopulmonary resuscitation by using only the force.

* * * * *